United States Patent [19]

Weigum et al.

[11] Patent Number: 4,950,295
[45] Date of Patent: Aug. 21, 1990

[54] BONE PROSTHESIS ANCHORING METHOD USING A RESORBABLE MARROW CAVITY CLOSURE

[75] Inventors: Hans Weigum; Robert Mathys, Jr., both of Bettlach, Switzerland

[73] Assignee: Robert Mathys Co., Bettlach, Switzerland

[21] Appl. No.: 341,917

[22] Filed: Apr. 24, 1989

[30] Foreign Application Priority Data

Apr. 22, 1988 [CH] Switzerland .......................... 1518/88

[51] Int. Cl.⁵ ............................. A61F 2/28; A61F 2/36
[52] U.S. Cl. ........................................ 623/16; 623/23; 606/77

[58] Field of Search ........................ 623/16, 16 A, 23; 128/92 YQ, 92 YG, 92 YR, 334 R, 92 VP

[56] References Cited

U.S. PATENT DOCUMENTS

| | | | |
|---|---|---|---|
| 4,186,448 | 2/1980 | Brekke | 623/16 |
| 4,302,855 | 12/1981 | Swanson | 623/16 A |
| 4,344,190 | 8/1982 | Lee et al. | 623/16 A |
| 4,745,914 | 5/1988 | Frey et al. | 623/16 X |

*Primary Examiner*—Ronald Frinks
*Attorney, Agent, or Firm*—Spencer & Frank

[57] ABSTRACT

A resorbable marrow cavity closure comprises a plug formed of randomly packed, crimped pieces of thread of a resorbable polymer material.

5 Claims, 1 Drawing Sheet

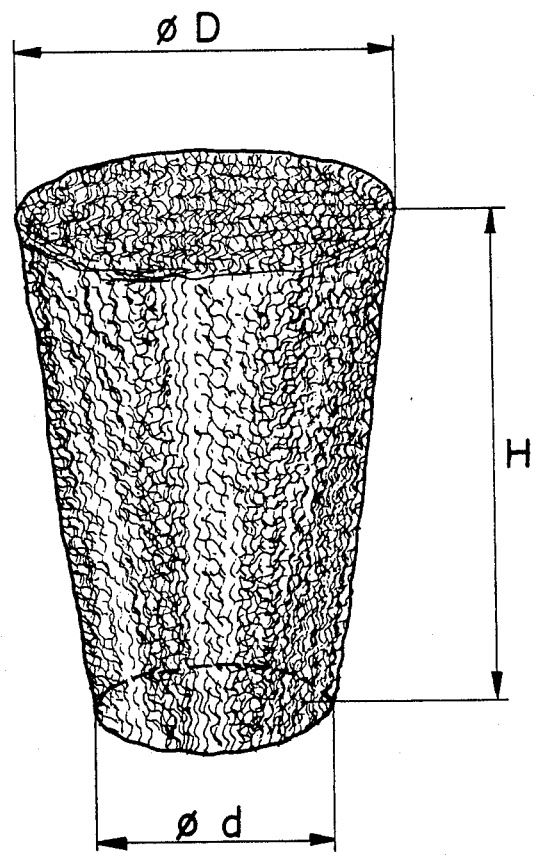

BONE PROSTHESIS ANCHORING METHOD USING A RESORBABLE MARROW CAVITY CLOSURE

BACKGROUND OF THE INVENTION

This invention relates to a closure for obturating a marrow cavity.

Hip joint prostheses are usually anchored in the marrow cavity of the femur by means of a bone cement composed of polymethyl methacrylate, introduced into the marrow cavity in a pasty form. Then the prosthesis shaft is pressed into the plastic mass and the cement is permitted to harden completely. Care must be taken that the bone cement is introduced into the marrow cavity to a depth which is just sufficient to allow the cement to reliably fill all of the area between the bone and the prosthesis shaft once the prosthesis shaft has been inserted. The pressure generated during the insertion of the prosthesis shaft is intended to compact the bone cement in order to maintain the formation of cavities due to the inclusion of air at a low level, and to cause the cement to better conform to the contours of the marrow cavity. This is more difficult if the still plastic cement is able to escape into the free marrow cavity during insertion of the prosthesis shaft.

To prevent an undesirable escape of bone cement, various closures for marrow cavities have been developed, namely those of endogenous materials (that is, bone spongiosa) and synthetic materials. Such a marrow cavity closure or block must be composed of body-compatible materials. Additionally, the closure should be deformable since, under certain circumstances, the closure must seal the marrow channel at a location beyond its narrowest point and usually at a location whose cross section deviates from the ideal circular shape. Moreover, it is advisable that the material not only be body-compatible but also resorbable by the body as quickly as possible since it no longer has any useful function once the cement has hardened which occurs in about 15 minutes.

Marrow cavity blocks made of bone spongiosa exhibit good body compatibility, they are quickly resorbed or transformed. A drawback of such blocks is that they are practically non-deformable and that they constitute a greater risk of infection compared to marrow cavity blocks made of synthetic materials because they can be disinfected only within limits. They also require a longer time for surgery, if they are made of bone material that is obtained during the same surgical procedure, for example, from the severed joint head.

Although the prior art marrow cavity blocks of synthetic materials, such as dextrose, are easily sterilized and are quickly resorbed by the body, due to their lack of deformability, they have only a limited sealing effect. These materials, to be sure, are able to swell, but the time available is too short to take advantage of this property.

SUMMARY OF THE INVENTION

It is an object of the invention to provide an improved marrow cavity closure which has all the advantages of prior art structures, but from which the discussed disadvantages are eliminated.

This object and others to become apparent as the specification progresses, are accomplished by the invention, according to which, briefly stated, the closure is a plug made of randomly packed, crinkled (crimped) thread lengths of a resorbable polymer material.

Advantageously, the thread pieces are monofilaments. According to an advantageous further feature of the invention, the plug is pressed to assume a frustoconical shape and fixed such that it is porous and elastically deformable. Expediently, the resorbable polymer material is a polylactic acid.

Because of the elastic deformability ensured by its configuration, the plug readily adapts itself to the shape and dimension of the marrow cavity, so that plugs of uniform size can be employed in most cases. Additionally, this configuration results in a selective blocking effect, making the plug impermeable to viscous substances, such as the bone cement, while it is permeable to air, rinsing liquids and blood, so that these substances can be displaced by the bone cement, causing fewer inclusions to be formed in the bone cement and at the interface between bone cement and bone, thus significantly increasing the quality of the hardened cement. The large specific surface area resulting from the plug construction according to the invention, particularly favors a rapid resorption.

BRIEF DESCRIPTION OF THE DRAWING

The sole FIGURE is a perspective view of a preferred embodiment of the invention.

DESCRIPTION OF THE PREFERRED EMBODIMENT

The sole FIGURE of the drawing depicts an embodiment of a marrow cavity block according to the present invention in the form of a plug which has the shape of a cone frustum. This plug has approximately the following dimensions: diameter at the base: D=about 15 mm; diameter at the top: d=about 10 mm; height: H=about 20 mm.

For preparing the plug, a filament, made, for example, of resorbable polymer material is wound on a mandrel and subsequently fixed by heating to obtain a crimped (crinkled) configuration. Or, as an alternative, crinkled fibers may be obtained by shaving a material block by a tool whose shape and cutting speed determine the desired crimped configuration.

Thereafter, the crimped fibers are cut into appropriate lengths, mixed and loosened and thereafter a desired quantity is placed in a pressing tool which lightly compresses the filament mass to determine the desired contour, in the present instance, a frustoconical shape.

By virtue of the appropriately selected filament diameter, crimp diameter, filament length and as a result of an appropriate loosening and mixing of the filament lengths, the material will be in the desired random orientation when it is placed into the pressing tool.

In the pressing tool, subsequent to the slight compression, the fiber material is submitted to heating whereby it is fixed in its desired shape.

It will be understood that the above description of the present invention is susceptible to various modifications, changes and adaptations, and the same are intended to be comprehended within the meaning and range of equivalents of the appended claims.

What is claimed is:

1. A method of anchoring a prosthesis in a marrow cavity of a bone, comprising the steps of blocking the marrow cavity by placing a porous plug formed of randomly packed, crimped pieces of thread of a resorbable polymer material into the marrow cavity to a depth sufficient to allow a cement to fill a portion of the marrow cavity between the bone and the prosthesis, filling the marrow cavity portion with cement, and inserting the prosthesis into the cement in the marrow cavity portion.

2. The method as defined in claim 1, wherein the plug is elastically deformable.

3. The method as defined in claim 1, wherein the plug is frustoconical.

4. The method as defined in claim 1, wherein the plug is made of polylactic acid.

5. The method as defined in claim 1, wherein the plug is made of monofilaments.

* * * * *